United States Patent [19]

Endo et al.

[11] Patent Number: 5,759,958
[45] Date of Patent: Jun. 2, 1998

[54] TRIAZOLE DERIVATIVE, HERBICIDAL COMPOSITIONS CONTAINING THE DERIVATIVES AND METHODS OF THEIR USE

[75] Inventors: Yoshinori Endo; Hirofumi Nakagawa, both of Tokushima; Hiroshi Fujishima, Naruto; Isao Tada, Tokushima; Minoru Motoki, Naruto; Daisuke Yanase, Naruto; Mitsuyuki Murakami, Naruto; Tatsuya Akasaka, Tokushima, all of Japan

[73] Assignee: Otsuka Kagaku Kabushiki Kaisha, Osaka, Japan

[21] Appl. No.: 817,916

[22] PCT Filed: Jan. 4, 1996

[86] PCT No.: PCT/JP96/00003

§ 371 Date: Apr. 25, 1997

§ 102(e) Date: Apr. 25, 1997

[87] PCT Pub. No.: WO97/09326

PCT Pub. Date: Mar. 13, 1997

[30] Foreign Application Priority Data

Sep. 7, 1995 [JP] Japan ................... 7-229876
Nov. 8, 1995 [JP] Japan ................... 7-289828
Nov. 28, 1995 [JP] Japan ................... 7-308657

[51] Int. Cl.$^6$ .............. A01N 43/653; C07D 405/04
[52] U.S. Cl. ............... 504/273; 548/263.2; 548/264.6
[58] Field of Search ................. 548/263.2, 264.6; 504/273

[56] References Cited

U.S. PATENT DOCUMENTS 5,108,486 4/1992 Kondo et al. ................... 71/92

Primary Examiner—Patricia L. Morris
Attorney, Agent, or Firm—Kubovcik & Kubovcik

[57] ABSTRACT

An object of the present invention is to provide a 1,2,4-triazole derivative which in a small amount exhibits high herbicidal activity against weeds in paddy fields, lawns or farmlands, the derivative being without injury to rice, turf grasses and crops. The 1,2,4-triazole derivative is represented by the formula

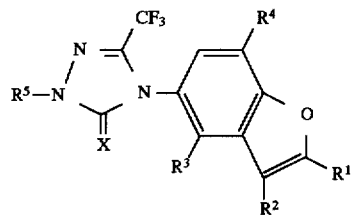

wherein $R^1$ and $R^2$ are the same or different and independently represent hydrogen or methyl, $R^3$ and $R^4$ are the same or different and independently represent halogen, lower alkyl, lower alkoxy, lower haloalkyl, lower haloalkoxy or cyano, $R^5$ represents methyl or ethyl and X represents oxygen or sulfur.

8 Claims, No Drawings

TRIAZOLE DERIVATIVE, HERBICIDAL COMPOSITIONS CONTAINING THE DERIVATIVES AND METHODS OF THEIR USE

FIELD OF THE INVENTION

The present invention relates to triazole derivatives, herbicidal compositions containing the derivatives and methods of their use.

BACKGROUND ART

Many herbicides are known today and some of them are widely used for weed control in agriculture.

U.S. Pat. No. 5,108,486 discloses that a certain type of 4-phenyl-1,2,4-triazole derivative has herbicidal activity and further illustrates some tests using the derivative under the conditions of farmlands. This derivative, however, does not exhibit high herbicidal activity against all kinds of weeds and no data on its selectivity, i.e., safety for crops are provided. Japanese Unexamined Patent Publication No. 188220/1995 discloses that 4-phenyl-1,2,4-triazole derivatives represented by the formula:

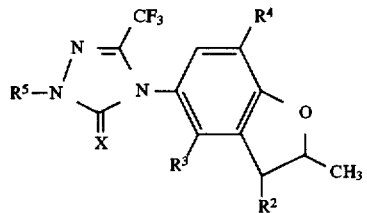

(wherein $R^2$ is hydrogen or methyl, $R^3$ and $R^4$ are both chlorine and $R^5$ is methyl or ethyl and X is oxygen or sulfur) have herbicidal activity against paddy weeds and are suitably used as herbicidal compositions for paddy fields. This type of triazole derivative has a dihydrobenzofuranone skeleton and does not cause any serious damage but is not totally safe for rice plants. Hence a need still exists for a safer compound. Furthermore, Japanese Unexamined Patent Publication No. 188220/1995 nowhere describes whether this triazole derivative has herbicidal activity against weeds in farmlands or lawns and merely teaches the activity against weeds in paddy fields.

DISCLOSURE OF THE INVENTION

An object of the invention is to provide a novel 1,2,4-triazole derivative having a benzofuran skeleton, which is neither described nor suggested in U.S. Pat. No. 5,108,486 or Japanese Unexamined Patent Publication No. 188220/1995.

Another object of the invention is to provide a herbicidal composition which in a small amount can exhibit high herbicidal activity against paddy weeds, the composition being without injury to rice.

Even another object of the invention is to provide a herbicidal composition which in a small amount can exhibit high herbicidal activity against turf weeds, the composition being without injury to the turf grasses.

A further object of the invention is to provide a herbicidal composition which in a very small amount can exhibit high herbicidal activity against upland weeds, the composition being without injury to crops and thus showing very high selectivity.

Also a further object of the invention is to provide a method for controlling the growth of undesired plants using the above-mentioned herbicidal composition.

Other features of the present invention will be apparent from the following description.

The 1,2,4-triazole derivatives of the invention are represented by the formula:

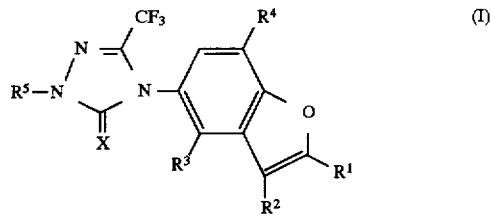

wherein $R^1$ and $R^2$ are the same or different and independently represent hydrogen or methyl, $R^3$ and $R^4$ are the same or different and independently represent halogen, lower alkyl, lower alkoxy, lower haloalkyl, lower haloalkoxy or cyano, $R^5$ represents methyl or ethyl and X represents oxygen or sulfur.

Specific examples of the groups represented by $R^3$ and $R^4$ in formula (I) are as follows.

Examples of the halogen atom are fluorine, chlorine, bromine and iodine.

Examples of the lower alkyl group are straight-chain or branched-chain alkyl groups of 1 to 6 carbon atoms such as methyl, ethyl, propyl, isopropyl, butyl, isobutyl, tert-butyl, pentyl, hexyl, etc.

Examples of the lower alkoxy group are straight-chain or branched-chain alkoxy groups of 1 to 6 carbon atoms, such as methoxy, ethoxy, propoxy, isopropoxy, butoxy, tert-butoxy, pentyloxy, hexyloxy, etc.

Examples of the lower haloalkyl group are straight-chain or branched-chain alkyl groups of 1 to 6 carbon atoms which have 1 to 3 halogen atoms as substituent(s), such as trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-bromopropyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, etc.

Examples of the lower haloalkoxy group are straight-chain or branched-chain alkoxy groups of 1 to 6 carbon atoms which have 1 to 3 halogen atoms as substituent(s), such as trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-bromopropoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, etc.

Of the compounds of the invention represented by formula (I), the following compounds are particularly preferred:

compounds of formula (I) wherein $R^1$ is methyl and $R^2$ is hydrogen;

compounds of formula (I) wherein $R^1$ is methyl and $R^3$ and $R^4$ are both halogen;

compounds of formula (I) wherein $R^1$ is methyl and $R^3$ and $R^4$ are both lower alkyl;

compounds of formula (I) wherein $R^1$ is methyl, $R^3$ is lower alkyl and $R^4$ is halogen;

compounds of formula (I) wherein $R^1$ is methyl, $R^3$ is halogen and $R^4$ is lower alkyl;

compounds of formula (I) wherein $R^1$ is methyl, $R^3$ is lower alkoxy and $R^4$ is halogen;

compounds of formula (I) wherein $R^1$ is methyl, $R^3$ is lower haloalkyl and $R^4$ is halogen;

compounds of formula (I) wherein $R^1$ is methyl, $R^3$ is cyano and $R^4$ is halogen; and compounds of formula (I) wherein $R^1$ is methyl, $R^3$ is halogen and $R^4$ is lower alkoxy.

The compounds of the invention represented by formula (I) can be prepared, for example, by the process illustrated below in Reaction Scheme-1:

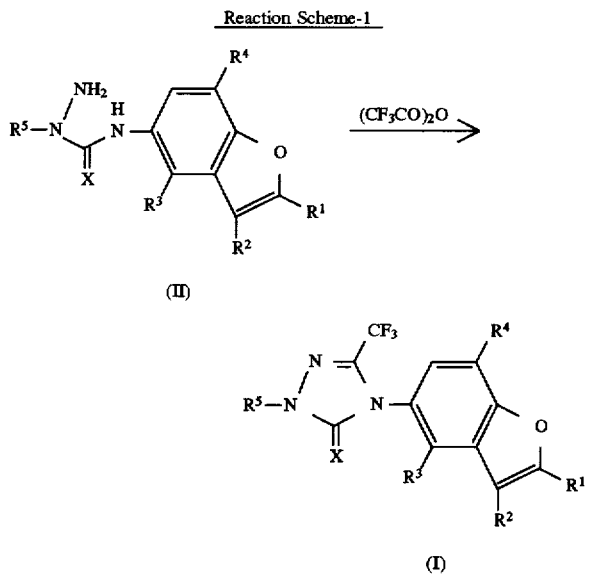

wherein $R^1$, $R^2$, $R^3$, $R^4$ and $R^5$ and X are as defined above.

According to Reaction Scheme-1, the compounds of the invention can be produced by reacting a (thio)semicarbazide (II) with trifluoroacetic anhydride in the absence of solvents or in the presence of a suitable solvent. Useful solvents include aromatic hydrocarbons such as benzene and toluene, halogenated hydrocarbons such as dichloromethane, 1,2-dichloroethane and chloroform, and mixtures thereof. There is no specific limitation on the ratio of (thio)semicarbazide (II) to trifluoroacetic anhydride but the latter is usually used in an amount of about 0.5 to about 3 moles, preferably about 1 to about 1.5 moles, per mole of the former. The reaction proceeds smoothly within a temperature range of room temperature to the boiling point of the solvent used. In the case of producing the compounds of formula (I) of the invention wherein X is oxygen, namely, oxo compounds, the reaction usually takes about 20–50 hours. In the case of the compounds of formula (I) wherein X is sulfur, namely, thiono compounds, the reaction is usually completed in about 1–5 hours. As regards the starting materials in Reaction Scheme-1, (thio)semicarbazide of formula (II) can be easily prepared from the corresponding aniline by a conventional method such as a method described in U.S. Pat. No. 4,514,419 or a method described in Synthesis-Stuttgart, (12), 923 (1989). The other starting material trifluoroacetic anhydride is commercially available easily.

The 1,2,4-triazole derivatives of the invention prepared by the foregoing process can be easily isolated and purified from the reaction mixture according to conventional isolation and purification methods.

The 1,2,4-triazole derivatives of the invention can selectively control gramineous plants such as Digitaria spp and Echinochloa spp, except Oryza spp, as well as broad-leaf weeds without showing any injury to rice plants, and therefore are highly effective in improving rice production by controlling harmful paddy weeds.

As the 1,2,4-triazole derivatives of the invention can also control selectively weeds infesting in the lawn without damaging the turf grass, these compounds are highly efficacious in controlling turf weeds in such locations as golf courses, parks, roads, graveyards, industrial sites, and gardens. In this specification, the term "turf grass" stands for Western turf grasses such as bent grass, bluegrass, and rye grass as well as traditional Japanese turf grasses such as Zoysia japonica and Zoysia matrella. The turf weeds include Poa annua, Digitaria ciliaris, Stellaria media, Cerastium glomeratum, etc.

The 1,2,4-triazole derivatives of the invention also show good selectivity for many upland crops while controlling weeds infesting in the farm. Such upland crops include maize, wheat, barley, oats, rye, soybean, cotton, and various vegetables. Herbicidal compositions containing a derivative of the invention as an active ingredient are particularly suited to be used for soybean, cotton, wheat, barley, oats, and rye. Upland weeds include Amaranthus retroflexus, Echinochloa crus-galli, Abutilon theophrasti, Rumex obtusifolius, Cyperus microirea, Arenaria serpyllifolia, Capsella bursa-pastoris, Lamium amplexicaule, Sonchus oleraceus, Poa annua, etc.

The compounds of the invention can be used as herbicidal compositions in various forms such as emulsifiable concentrate, wettable powder, water dispersible granule, suspension concentrate, soluble concentrate, granule, fine granule, granule, dustable powder, coating paste, spray preparation, aerosol, capsule suspension, fumigant, smoking agent, etc.

Examples of adjuvants for the herbicidal compositions of the invention are extenders such as diatomaceous earth, kaolin, clay, bentonite, white carbon and talc; nonionic surfactants such as polyoxyethylene alkyl ethers, polyoxyethylene alkyl esters and polyoxyethylene sorbitan alkyl esters; and anionic surfactants such as alkylbenzenesulfonates, alkyl sulfosuccinates, alkyl sulfates, polyoxyethylene alkyl sulfates, alkylsulfonates, arylsulfonates and lignin sulfites.

Examples of solvents or diluents incorporated in the herbicidal compositions of the invention are water, various types of organic solvents, aerosol propellants, natural minerals and synthetic compounds, etc. Examples of preferred organic solvents are benzene, toluene, xylene, ethylbenzene, chlorobenzene, alkylnaphthalene, chloroethylene, cyclohexanone, methyl ethyl ketone, methyl isobutyl ketone, alcohols, cellosolves, dimethylformamide, dimethylsulfoxide, acetonitrile, mineral oil distillate, etc. Examples of useful aerosol propellants are propane, butane, halogenated hydrocarbons, nitrogen, carbon dioxide, etc.

The herbicidal compositions of the invention may be colored with an organic or inorganic dye.

In the present invention, the above-mentioned various forms of the composition are prepared in a manner to incorporate the compound of the invention in an amount of about 0.1 to about 95% by weight, preferably about 0.5 to about 90% by weight. The composition thus formed is used as such or as diluted with a carrier or water. In conformity with the contemplated purpose, the composition can be diluted to the range that the compound of the invention accounts for about 0.0001 to about 100% by weight, preferably about 0.001 to about 10% by weight, of the dilution.

The herbicidal compositions of the invention can be used in combination with other herbicides, fungicides or insecticides, also.

The herbicidal compositions of the invention can control the growth of weeds. Paddy weeds include the above-mentioned broad-leaf weeds and gramineous plants, except *Oryza sativa*, such as Digitaria spp. and Echinochloa spp. and turf weeds include *Poa annua, Digitaria ciliaris, Stellaria miedia, Cerastium glomeratum*, etc. Upland weeds include *Amaranthus retroflexus, Echinochloa crus-galli, Abutilon theophrasti, Rumex obtusifolius, Cyperus microiria, Arenaria serpyilifolia, Capsella bursa-pastoris, Lamium amplexicaule, Sonchus oleraeus, Poa annua*, etc.

There is no specific limitation on the method of using the herbicidal compositions of the invention to control the growth of paddy weeds. However, the water treatment for paddy fields is preferably used. For example, four to six days after rice planting, the herbicidal compositions of the invention are applied to the flooding rice paddy to control the weeds therein.

To control the growth of weeds in paddy fields, lawns or farmlands, the herbicidal compositions of the invention are used in an amount of 1–1000 g/10a, preferably 10–100 g /10a, calculated as the 1,2,4-triazole derivative of formula (I).

BEST MODE FOR CARRYING OUT THE INVENTION

The following preparation examples, formulation examples and test examples are further illustrative of the present invention. In the formulation examples, parts are by weight unless otherwise specified.

PREPARATION EXAMPLE 1

Preparation of the compound of formula (I) wherein $R^1$ is methyl, $R^2$ is hydrogen, $R^3$ is methyl, $R^4$ is isopropyl, $R^5$ is methyl and X is oxygen (compound 1).

Trifluoroacetic anhydride (20 mmol) was added dropwise to a suspension of 12 mmol of semicarbazide in 30 ml of toluene cooling with an ice-water bath. After completion of addition, the reaction mixture was stirred at room temperature for another 30 hours. The reaction mixture was washed with 10% aqueous sodium carbonate solution and dried over anhydrous magnesium sulfate. The solvent was distilled off. The residue was purified by silica gel chromatography (eluent=hexane:ethyl acetate=2:1) to provide 2.12 g of the title compound (compound 1).

m.p.: 122°–123° C.

$^1$H-NMR (CDCl$_3$; δ ppm) 1.32 (6H), 2.12 (3H), 2.46 (3H), 3.39 (1H), 3.58 (3H), 6.37 (1H), 6.83 (1H)

The above results confirmed that the obtained white crystals were the title compound.

The compounds shown below in Tables 1 and 2 were prepared in the same manner as in Preparation Example 1, using appropriate starting materials.

TABLE 1

| Preparation Example No. | $R^1$ | $R^2$ | $R^3$ | $R^4$ | $R^5$ | X |
|---|---|---|---|---|---|---|
| 2 | Me | H | Cl | Cl | Me | S |
| 3 | Me | Me | Cl | Cl | Me | S |
| 4 | Me | H | Cl | Me | Me | S |
| 5 | Me | H | Me | Cl | Me | S |
| 6 | Me | H | Me | Cl | Me | O |
| 7 | Me | H | Me | Br | Me | S |
| 8 | Me | H | Me | Br | Me | O |
| 9 | Me | H | CF$_3$ | Cl | Me | S |
| 10 | Me | H | CF$_3$ | Cl | Me | O |
| 11 | Me | H | Me | Me | Me | S |
| 12 | Me | H | CN | Cl | Me | S |
| 13 | Me | H | Me | Me | Me | O |
| 14 | Me | Me | Cl | Cl | Me | O |

TABLE 1-continued

| Preparation Example No. | $R^1$ | $R^2$ | $R^3$ | $R^4$ | $R^5$ | X |
|---|---|---|---|---|---|---|
| 15 | Me | H | Cl | Cl | Me | O |
| 16 | H | Me | Cl | Cl | Me | S |
| 17 | H | Me | Cl | Cl | Me | O |
| 18 | H | H | Cl | Cl | Et | S |
| 19 | H | H | Cl | Cl | Me | O |
| 20 | Me | H | Me | iPr | Me | S |

Notes:
Me: methyl
Et: ethyl
iPr: isopropyl

TABLE 2

| Preparation Example No. | $R^1$ | $R^2$ | $R^3$ | $R^4$ | $R^5$ | X |
|---|---|---|---|---|---|---|
| 21 | Me | H | Cl | Me | Me | O |
| 22 | Me | H | OMe | Cl | Me | S |
| 23 | Me | H | OMe | Cl | Me | O |
| 24 | Me | H | Me | F | Me | S |
| 25 | Me | H | Me | F | Me | O |
| 26 | Me | H | F | Cl | Me | S |
| 27 | Me | H | F | Cl | Me | O |
| 28 | Me | Me | F | Cl | Me | S |
| 29 | Me | Me | F | Cl | Me | O |
| 30 | Me | H | CF$_3$ | Cl | Et | S |
| 31 | Me | H | CF$_3$ | Cl | Et | O |
| 32 | H | H | Me | Me | Me | S |
| 33 | H | H | Me | Me | Me | O |
| 34 | Me | H | iPr | Me | Me | S |
| 35 | Me | H | iPr | Me | Me | O |
| 36 | Me | H | iPr | Cl | Me | S |
| 37 | Me | H | Me | OMe | Me | S |
| 38 | Me | H | OCF$_3$ | Cl | Me | S |
| 39 | Me | H | Me | tBu | Me | O |

Notes:
Me: methyl
OMe: methoxy
Et: ethyl
iPr: isopropyl
tBu: tert-butyl

Given below are physical properties of the compounds obtained in Preparation Examples and shown above in Tables 1 and 2.

COMPOUND OF PREPARATION EXAMPLE 2 m.p.: 113°–114° C.

$^1$H-NMR (CDCl$_3$) δ ppm; 2.56 (3H), 3.92 (3H), 6.63 (1H), 7.22 (1H)

COMPOUND OF PREPARATION EXAMPLE 3 m.p.: 104°–105° C.

$^1$H-NMR (CDCl$_3$) δ ppm; 2.35, 2.42 (6H), 3.89 (3H), 7.22 (1H)

COMPOUND OF PREPARATION EXAMPLE 4 m.p.: 124°–125° C.

$^1$H-NMR (CDCl$_3$) δ ppm; 2.48 (6H), 3.87 (3H), 6.47 (1H), 7.06 (1H)

COMPOUND OF PREPARATION EXAMPLE 5 m.p.: 127°–128° C.

$^1$H-NMR (CDCl$_3$) δ ppm; 2.15 (3H), 2.53 (3H), 3.88 (3H), 6.47 (1H), 7.02 (1H)

COMPOUND OF PREPARATION EXAMPLE 6 m.p.: 136°–137° C.

$^1$H-NMR (CDCl$_3$) δ ppm; 2.20 (3H), 2.74 (3H), 3.57 (3H), 6.42 (1H), 7.02 (1H)

COMPOUND OF PREPARATION EXAMPLE 7 m.p.: 121°–122° C.

$^1$H-NMR (CDCl$_3$) δ ppm; 2.18 (3H), 2.52 (3H), 3.90 (3H), 6.50 (1H), 7.18 (1H)

COMPOUND OF PREPARATION EXAMPLE 8 m.p.: 145°–146° C.

$^1$H-NMR (CDCl$_3$) δ ppm; 2.20 (3H), 2.50 (3H), 3.58 (3H), 6.48 (1H), 7.20 (1H)

COMPOUND OF PREPARATION EXAMPLE 9 m.p.: 88°–91° C.

$^1$H-NMR (CDCl$_3$) δ ppm; 2.55 (3H), 3.85 (3H), 6.70 (1H), 7.15 (1H)

COMPOUND OF PREPARATION EXAMPLE 10 m.p.: 85°–88° C.

$^1$H-NMR (CDCl$_3$) δ ppm; 2.54 (3H), 3.57 (3H), 6.70 (1H), 7.23 (1H)

COMPOUND OF PREPARATION EXAMPLE 11 m.p.: 107°–108° C.

$^1$H-NMR (CDCl$_3$) δ ppm; 2.15 (3H), 2.44 (6H), 3.70 (3H), 6.37 (1H), 6.75 (1H)

COMPOUND OF PREPARATION EXAMPLE 12 viscous liquid $^1$H-NMR (CDCl$_3$) δ ppm; 2.60 (3H), 3.90 (3H), 6.75 (1H), 7.25 (1H)

COMPOUND OF PREPARATION EXAMPLE 13 m.p.: 90°–91° C.

$^1$H-NMR (CDCl$_3$) δ ppm; 2.18 (3H), 2.45 (6H), 3.55 (3H), 6.33 (1H), 6.75 (1H)

COMPOUND OF PREPARATION EXAMPLE 14 m.p.: 109°–110° C.

$^1$H-NMR (CDCl$_3$) δ ppm; 2.35, 2.42 (6H), 3.62 (3H), 7.24 (1H)

COMPOUND OF PREPARATION EXAMPLE 15 m.p.: 115°–116° C.

$^1$H-NMR (CDCl$_3$) δ ppm; 2.56 (3H), 3.63 (3H), 6.60 (1H), 7.24 (1H)

COMPOUND OF PREPARATION EXAMPLE 16 m.p.: 111°–112° C.

$^1$H-NMR (CDCl$_3$) δ ppm; 2.52 (3H), 3.90 (3H), 7.24 (1H), 7.40 (1H)

COMPOUND OF PREPARATION EXAMPLE 17 m.p.: 114°–115° C.

$^1$H-NMR (CDCl$_3$) δ ppm; 2.52 (3H), 3.90 (3H), 7.24 (1H), 7.40 (1H)

COMPOUND OF PREPARATION EXAMPLE 18 m.p.: 113°–114° C.

$^1$H-NMR (CDCl$_3$) δ ppm; 1.30 (3H), 3.86 (2H), 6.30 (1H), 7.24 (1H), 7.40 (1H)

COMPOUND OF PREPARATION EXAMPLE 19 m.p.: 127°–128° C.

$^1$H-NMR (CDCl$_3$) δ ppm; 3.60 (3H), 6.30 (1H), 7.24 (1H), 7.40 (1H)

COMPOUND OF PREPARATION EXAMPLE 20 m.p.: 114°–115° C.

$^1$H-NMR (CDCl$_3$) δ ppm; 1.32 (6H), 2.15 (3H), 2.46 (3H), 3.38 (1H), 3.87 (3H), 6.40 (1H), 6.77(1H)

COMPOUND OF PREPARATION EXAMPLE 21 m.p.: 93°–94° C.

$^1$H-NMR (CDCl$_3$) δ ppm; 2.46 (6H), 3.56 (3H), 6.42 (1H), 6.92 (1H)

COMPOUND OF PREPARATION EXAMPLE 22 m.p.: 142°–143° C.

$^1$H-NMR (CDCl$_3$) δ ppm; 2.52 (3H), 3.88 (3H), 4.00 (3H), 6.65 (1H), 7.05 (1H)

COMPOUND OF PREPARATION EXAMPLE 23 m.p.: 189°–190° C.

$^1$H-NMR (CDCl$_3$) δ ppm; 2.50 (3H), 3.58 (3H), 4.00 (3H), 6.60 (1H), 7.05 (1H)

COMPOUND OF PREPARATION EXAMPLE 24 m.p.: 129°–130° C.

$^1$H-NMR (CDCl$_3$) δ ppm; 2.15 (3H), 2.48 (3H), 3.88 (3H), 6.46 (1H), 6.76 (1H)

COMPOUND OF PREPARATION EXAMPLE 25 m.p.: 147°–148° C.

$^1$H-NMR (CDCl$_3$) δ ppm; 2.20 (3H), 2.49 (3H), 3.57 (3H), 6.47 (1H), 6.80 (1H)

COMPOUND OF PREPARATION EXAMPLE 26 m.p.: 80°–81° C.

$^1$H-NMR (CDCl$_3$) δ ppm; 2.52 (3H), 3.88 (3H), 6.60 (1H), 7.15 (1H)

COMPOUND OF PREPARATION EXAMPLE 27 m.p.: 132°–133° C.

$^1$H-NMR (CDCl$_3$) δ ppm; 2.51 (3H), 3.58 (3H), 6.55 (1H), 7.13 (1H)

COMPOUND OF PREPARATION EXAMPLE 28 viscous liquid $^1$H-NMR (CDCl$_3$) δ ppm; 2.33 (3H), 2.40 (3H), 3.86 (3H), 7.15 (1H)

COMPOUND OF PREPARATION EXAMPLE 29 m.p.: 109°–113° C.

$^1$H-NMR (CDCl$_3$) δ ppm; 2.32 (3H), 2.40 (3H), 3.57 (3H), 7.13 (1H)

COMPOUND OF PREPARATION EXAMPLE 30 viscous liquid $^1$H-NMR (CDCl$_3$) δ ppm; 1.50 (3H), 2.58 (3H), 4.30 (2H), 6.70 (1H), 7.14 (1H)

COMPOUND OF PREPARATION EXAMPLE 31 viscous liquid $^1$H-NMR (CDCl$_3$) δ ppm; 1.46 (3H), 2.51 (3H), 3.96 (2H), 6.59 (1H), 7.21 (1H)

COMPOUND OF PREPARATION EXAMPLE 32 viscous liquid $^1$H-NMR (CDCl$_3$) δ ppm; 2.14 (3H), 2.44 (3H), 3.69 (3H), 6.34 (1H), 6.75 (1H), 7.38 (1H)

COMPOUND OF PREPARATION EXAMPLE 33 viscous liquid $^1$H-NMR (CDCl$_3$) δ ppm; 2.16 (3H), 2.44 (3H), 3.55 (3H), 6.32 (1H), 6.74 (1H), 7.36 (1H)

COMPOUND OF PREPARATION EXAMPLE 34 m.p.: 128°–129° C.

$^1$H-NMR (CDCl$_3$) δ ppm; 1.23–1.48 (6H), 2.46 (6H), 2.63 (3H), 3.88 (3H), 6.60 (1H), 6.69 (1H)

COMPOUND OF PREPARATION EXAMPLE 35 m.p.: 144°–145° C.

$^1$H-NMR (CDCl$_3$) δ ppm; 1.25–1.42 (6H), 2.45 (3H), 2.47 (3H), 2.77 (1H), 3.59 (3H), 6.58 (1H), 6.78(1H)

COMPOUND OF PREPARATION EXAMPLE 36 m.p.: 124°–125° C.

$^1$H-NMR (CDCl$_3$) δ ppm; 1.22–1.58 (6H), 2.50 (3H), 2.60 (1H), 3.90 (3H), 6.70 (1H), 7.00 (1H)

COMPOUND OF PREPARATION EXAMPLE 37 viscous liquid $^1$H-NMR (CDCl$_3$) δ ppm; 2.25 (3H), 2.45 (3H), 3.59 (3H), 3.95 (3H), 6.35 (1H), 6.53 (1H)

COMPOUND OF PREPARATION EXAMPLE 38 viscous liquid $^1$H-NMR (CDCl$_3$) δ ppm; 2.52 (3H), 3.88 (3H), 6.65 (1H), 7.03 (1H)

COMPOUND OF PREPARATION EXAMPLE 39 m.p.: 124°–125° C.

$^1$H-NMR (CDCl$_3$) δ ppm; 1.50 (9H), 2.20 (3H), 2.45 (3H), 3.55 (3H), 6.35 (1H), 6.80 (1H)

Formulation Example 1 (10% wettable powder)

| | |
|---|---|
| Compound of formula (I) | 10.0 parts |
| Zeaklite (kaolin-type clay; product of Zeaklite Industry, Co., Ltd.) | 87.3 parts |
| SORPOL 800 A | 1.35 parts |
| RUNOX P-65-L (product of Toho Chemical Industry, Co., Ltd.) | 1.35 parts |

Formulation Example 2 (10% suspension concentrate)

| | |
|---|---|
| Compound of formula (I) | 10.0 parts |
| KP-1436 (25) (product of Kao Corporation) | 10.0 parts |
| RUNOX 100C (product of Toho Chemical Industry, Co., Ltd.) | 0.5 part |
| 1% RHODOPOL solution (product of Rhône-Poulenc) | 40.0 parts |
| Water | 39.5 parts |

Test Example 1 (Pre-emergence application in the paddy condition)

Pots, 8.5 cm across (9.2 cm in outside diameter) and 9.0 cm deep, were filled with clay loam, containing an appropriate amount of a fertilizer mixture and saturated with water in a mixer to reach suitable fluidity. Seeds of *Echinochloa oryzicola, Scirpus juncoides*, broad-leaf weeds (*Rotala indica* and *Lindernia pyxidaria*), *Cyperus difformis* and *Monochoria vaginalis* were sown on the soil surface. Then, after the soil surface was gently press-levelled, rice seedlings (cultivar: Akinishiki) at the two-leaf stage were transplanted into the pots and the water depth was adjusted to 3 cm. Three days later, the test compounds were applied in a predetermined amount calculated as the active ingredient by pipetting solutions of the wettable powder, prepared according to the Formulation Example 1, uniformly onto the water surface. Three weeks after treatment, herbicidal injuries to rice and weeds were rated by the criteria given below. The results were presented in Table 3. The compound No. in Table 3 corresponds to that in the section "Preparation Examples". As the reference herbicide mefenacet (2-benzothiazol-2-yloxy-N-methylacetanilide, hereafter referred to as "compound A") was likewise tested, and the results were included in Table 3.

Criteria

5: complete killing.

4.5: 90–100% control.

4: 70–90% control.

3: 40–70%. control.

2: 20–40% control.

1: 0–20% control.

0: no injury.

TABLE 3

| Compound No. | Rate (g/10a) | Plants | | | | | |
|---|---|---|---|---|---|---|---|
| | | A | B | C | D | E | F |
| 2 | 20 | 0 | 5 | 4 | 3 | 4 | 5 |
| 3 | 20 | 0 | 5 | 4 | 3 | 4 | 4 |
| 4 | 20 | 0 | 5 | 4 | 4 | 4 | 4 |
| 5 | 20 | 0 | 5 | 4 | 3 | 4 | 5 |
| 6 | 20 | 0 | 5 | 4.5 | 4 | 4 | 5 |
| 7 | 20 | 0 | 5 | 4.5 | 4 | 4 | 5 |
| 9 | 20 | 0 | 5 | 4 | 4 | 4 | 4 |
| 12 | 20 | 0 | 5 | 3 | 3 | 4 | 4 |
| 14 | 20 | 0 | 5 | 4 | 3 | 4 | 4.5 |
| 15 | 20 | 0 | 5 | 4.5 | 4 | 4 | 4 |
| 16 | 20 | 0 | 5 | 4 | 3 | 4 | 5 |
| 17 | 20 | 0 | 5 | 4 | 3 | 4 | 4.5 |
| 18 | 20 | 0 | 5 | 4 | 4 | 4 | 4 |
| 19 | 20 | 0 | 5 | 3 | 3 | 4 | 4 |

TABLE 3-continued

| Compound No. | Rate (g/10a) | Plants | | | | | |
|---|---|---|---|---|---|---|---|
| | | A | B | C | D | E | F |
| 20 | 20 | 0 | 5 | 4 | 4 | 4 | 5 |
| 21 | 20 | 0 | 5 | 4 | 4 | 4 | 4.5 |
| 24 | 20 | 0 | 5 | 4.5 | 4 | 4 | 4 |
| A | 20 | 0 | 5 | 2 | 3 | 4 | 3 |

Notes:
A: Rice
B: *Echinochloa oryzicola*
C: Broad-leaf
D: *Scirpus juncoides*
E: *Cyperus difformis*
F: *Monochoria vaginalis*

Test Example 2 (Herbicidal activity against turf weeds)

Clay loam and a proper quantity of a fertilizer mixture were placed in pots. As test plants, seeds of *Digitaria ciliaris, Poa annua, Echinochloa oryzicola, Stellaria media* and *Cerastium glomeratum* were sown therein and covered with small amounts of soil. The test compounds were formed into 10% suspension concentrates according to Formulation Example 2 and 1000-fold diluted with water. The aqueous solutions were applied in an amount of 30 g/10a, calculated as the test compound, uniformly onto the soil. The test plants were grown absorbing water from beneath. The herbicidal efficacy of the test compounds was visually evaluated according to the criteria indicated in Test Example 1 every week. The results of 3 weeks after application were presented in Table 2. Compound No. in Table 4 corresponds to Preparation Example No. For comparison, the compound of the formula

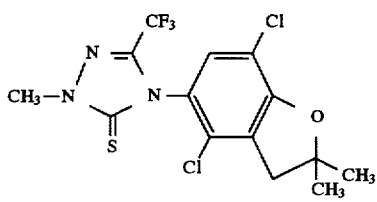

(described in U.S. Pat. No. 5,108,486; hereinafter referred to as "compound B") and the compound of the formula

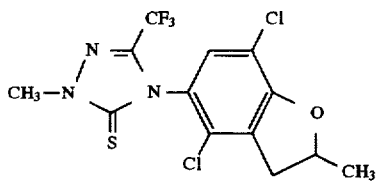

(described in Japanese Unexamined Patent Publication No. 188220/1995; hereinafter referred to as "compound C") were likewise tested for their herbicidal efficacy, and the results were included in Table 4.

TABLE 4

| Compound No. | Plants | | | | |
|---|---|---|---|---|---|
| | G | H | I | J | K |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |
| 7 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| B | 3 | 2 | 3 | 2 | 2 |
| C | 3 | 3 | 4 | 3 | 3 |

Notes:
G: *Digitaria ciliaris*
H: *Poa annua*
I: *Echinochloa oryzicola*
J: *Stellaria media*
K: *Cerastium glomeratum*

Test Example 3 (Safety for turf grasses)

(1) *Zoysia matrella*

A mixture of coarse sand and clay loam (1:1) was placed in pots 15 cm in diameter. *Zoysia matrella* was cut to the diametric size of the pots and planted therein. One month later, after confirming that the turf was deeply rooted in the pots and cutting the turf grass to about 1 cm above ground, 10% suspension concentrates prepared using the test compounds according to Formulation Example 2 and 500-fold diluted with water were applied in an amount of 100 g/10a, calculated as the test compound, uniformly over the turf. After treatment with the test compounds, the turf grass was grown for one month, followed by checking the adverse effect of each test compound on the growth of the turf grass. The injury of the test compounds to the turf grass was evaluated according to the criteria indicated in Test Example 1.

(2) Bent grass

A mixture of coarse sand and clay loam (1:1) was placed in pots 15 cm in diameter. Bent grass was seeded and cultivated for 2 months during which the turf grass was cut twice. One day before application of test compounds, grown stems and leaves of the grass were cut to 1 cm above ground. The treatment with the test compounds and evaluation of their injury were performed in the same manner as in the *Zoysia poatrella* test.

The results are shown in Table 5.

TABLE 5

| Compound No. | *Zoysia matrella* | Bent grass |
|---|---|---|
| 1 | 0 | 0 |
| 2 | 0 | 0 |
| 3 | 0 | 0 |
| 4 | 0 | 1 |
| 7 | 0 | 0 |
| 10 | 0 | 1 |
| 11 | 0 | 0 |

Test Example 4 (Herbicidal activity against upland weeds)

Clay loam and a proper quantity of a fertilizer mixture were placed in pots. As test plants, seeds of *Amaranthus retroflexus, Echinochloa crus-galli, Abutilon theophrasti, Rumex obtusifolius, Cyperus microiria, Arenaria serpyllifolia, Capsella bursa-pastoris, Lamium*

*amplexicaule, Sonchus oleraeus, Poa annua*, soybean, cotton and wheat were sown therein and covered with small amounts of soil. The test compounds were formed into 10% suspension concentrates according to Formulation Example 2 and 1000-fold diluted with water. The aqueous solutions were applied in an amount of 50 g/10a, calculated as the test compound, uniformly onto the soil. The test plants were grown absorbing water from beneath. The herbicidal efficacy of the test compounds was checked with unaided eye every week and evaluated according to the criteria indicated in Test Example 1. The results of 3 weeks after application were presented in Tables 6 and 7 below. Compound No. in Tables 6 and 7 corresponds to Preparation Example No. For comparison, compounds B and C were likewise tested for their herbicidal efficacy, and the results were included in Tables 6 and 7.

TABLE 6

| Compound No. | Plants | | | | | | |
|---|---|---|---|---|---|---|---|
| | L | M | N | O | P | Q | R |
| 1 | 5 | 4 | 5 | 5 | 5 | 5 | 5 |
| 2 | 5 | 4 | 5 | 5 | 5 | 4 | 5 |
| 3 | 5 | 5 | 5 | 5 | 5 | 5 | 5 |
| 4 | 5 | 4 | 5 | 5 | 5 | 5 | 4 |
| 5 | 5 | 5 | 5 | 5 | 5 | 5 | 4 |
| 6 | 5 | 5 | 5 | 5 | 5 | 5 | 5 |
| 7 | 5 | 4 | 5 | 5 | 5 | 5 | 5 |
| 8 | 5 | 5 | 5 | 5 | 5 | 5 | 5 |
| 9 | 5 | 5 | 5 | 5 | 5 | 5 | 4 |
| 10 | 5 | 4 | 5 | 5 | 5 | 5 | 5 |
| 11 | 5 | 4 | 5 | 5 | 5 | 5 | 5 |
| 12 | 5 | 4 | 5 | 5 | 5 | 5 | 5 |
| B | 3 | 2 | 3 | 4 | 4 | 3 | 3 |
| C | 3 | 2 | 4 | 3 | 4 | 3 | 3 |

Notes:
L: *Amaranthus retroflexus*
M: *Abutilon theophrasti*
N: *Rumex obtusifolius*
O: *Arenaria serpyllifolia*
P: *Capsella bursa-pastoris*
Q: *Lamium amplexicaule*
R: *Sonchus oleraeus*

TABLE 7

| Compound No. | Plants | | | | | |
|---|---|---|---|---|---|---|
| | S | T | U | V | W | X |
| 1 | 5 | 5 | 5 | 0 | 0 | 0 |
| 2 | 5 | 5 | 5 | 0 | 1 | 0 |
| 3 | 5 | 5 | 5 | 0 | 0 | 1 |
| 4 | 5 | 5 | 5 | 0 | 0 | 0 |
| 5 | 5 | 5 | 5 | 0 | 0 | 0 |
| 6 | 5 | 5 | 5 | 0 | 0 | 0 |
| 7 | 5 | 5 | 5 | 0 | 1 | 0 |
| 8 | 5 | 5 | 5 | 0 | 1 | 1 |
| 9 | 5 | 5 | 5 | 0 | 0 | 0 |
| 10 | 5 | 5 | 5 | 0 | 1 | 0 |
| 11 | 5 | 5 | 5 | 0 | 1 | 0 |
| 12 | 5 | 5 | 5 | 0 | 1 | 0 |
| B | 3 | 3 | 4 | 1 | 2 | 2 |
| C | 3 | 3 | 3 | 1 | 1 | 1 |

Notes:
S: *Echinochloa crus-galli*
T: *Poa annua*
U: *Cyperus microiria*
V: Cotton
W: Soybean
X: Wheat

We claim:

1. A 1,2,4-triazole derivative of the formula:

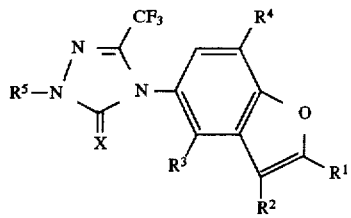

wherein $R^1$ and $R^2$ are the same or different and independently represent hydrogen or methyl, $R^3$ and $R^4$ are the same or different and independently represent halogen, lower alkyl, lower alkoxy, lower haloalkyl, lower haloalkoxy or cyano, $R^5$ represents methyl or ethyl and X represents oxygen or sulfur.

2. A 1,2,4-triazole derivative according to claim 1 wherein $R^3$ and $R^4$ are both chlorine.

3. A 1,2,4-triazole derivative according to claim 1 wherein $R^3$ and $R^4$ are not both chlorine.

4. A herbicidal composition comprising an inert carrier and, as an active ingredient, a herbicidally effective amount of a 1,2,4-triazole derivative of the formula:

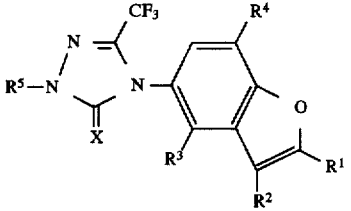

wherein $R^1$ and $R^2$ are the same or different and independently represent hydrogen or methyl, $R^3$ and $R^4$ are the same or different and independently represent halogen, lower alkyl, lower alkoxy, lower haloalkyl, lower haloalkoxy or cyano, $R^5$ represents methyl or ethyl and X represents oxygen or sulfur.

5. A method for controlling the growth of undesired plants using a herbicidal composition comprising an inert carrier and, as an active ingredient, a herbicidally effective amount of a 1,2,4-triazole derivative of the formula:

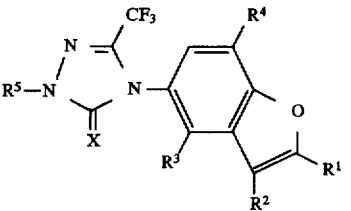

wherein $R^1$ and $R^2$ are the same or different and independently represent hydrogen or methyl, $R^3$ and $R^4$ are the same or different and independently represent halogen, lower alkyl, lower alkoxy, lower haloalkyl, lower haloalkoxy or cyano, $R^5$ represents methyl or ethyl and X represents oxygen or sulfur, the herbicidal composition being used in an amount of 1–1000 g/10a, calculated as the 1,2,4-triazole derivative.

6. A method according to claim 5 wherein the undesired plants are paddy weeds.

7. A method according to claim 5 wherein the undesired plants are turf weeds.

8. A method according to claim 5 wherein the undesired plants are upland weeds.

* * * * *